(12) United States Patent
Oldoni et al.

(10) Patent No.: US 9,522,127 B2
(45) Date of Patent: *Dec. 20, 2016

(54) USE OF HISTONE DEACETYLASE INHIBITORS FOR THE CARE OF PHILADELPHIA-NEGATIVE MYELOPROLIFERATIVE SYNDROMES

(71) Applicant: ITALFARMACO SPA, Milan (IT)

(72) Inventors: Tiziano Oldoni, Rho (IT); Paolo Mascagni, Villasanta (IT); Alessandro Rambaldi, Bergamo (IT); Tiziano Barbui, Bergamo (IT)

(73) Assignee: ITALFARMACO SPA, Milan (IT)

( * ) Notice: Subject to any disclaimer, the term of this patent is extended or adjusted under 35 U.S.C. 154(b) by 15 days.

This patent is subject to a terminal disclaimer.

(21) Appl. No.: 14/047,391

(22) Filed: Oct. 7, 2013

(65) Prior Publication Data
US 2014/0039059 A1 Feb. 6, 2014

Related U.S. Application Data

(60) Division of application No. 13/064,450, filed on Mar. 25, 2011, now abandoned, which is a continuation of application No. PCT/EP2009/062214, filed on Sep. 21, 2009.

(60) Provisional application No. 61/193,283, filed on Nov. 13, 2008.

(51) Int. Cl.
| | |
|---|---|
| A61K 31/00 | (2006.01) |
| A61K 31/16 | (2006.01) |
| A61K 31/167 | (2006.01) |
| A61K 45/06 | (2006.01) |
| A61K 31/18 | (2006.01) |

(52) U.S. Cl.
CPC ............ *A61K 31/167* (2013.01); *A61K 31/00* (2013.01); *A61K 31/16* (2013.01); *A61K 31/18* (2013.01); *A61K 45/06* (2013.01)

(58) Field of Classification Search
CPC ...... A61K 31/00; A61K 31/16; A61K 31/167; A61K 45/06
See application file for complete search history.

(56) References Cited

U.S. PATENT DOCUMENTS

2009/0088410 A1  4/2009  Zeldis

FOREIGN PATENT DOCUMENTS

| EP | 0 847 992 A1 | 6/1998 |
|---|---|---|
| WO | WO 93/07148 A1 | 4/1993 |
| WO | WO 97/43251 A1 | 11/1997 |
| WO | WO 2004/065355 A1 | 8/2004 |
| WO | WO 2004/071400 A2 | 8/2004 |
| WO | WO 2006/063294 A2 | 6/2006 |
| WO | WO 2007/016354 A1 | 2/2007 |
| WO | WO 2007/067795 A2 | 6/2007 |
| WO | WO 2008/058287 A1 | 5/2008 |
| WO | WO 2008/082646 A2 | 7/2008 |

OTHER PUBLICATIONS

Golay et al. "The histone deacetylase inhibitor ITF2357 has anti-leukemic activity in vito and inhibits IL-6 and VEGF production by stromal cells" Leukemia, 2007, vol. 21, pp. 1892-1900.*
Galli, Monica, et al; "A phase II multiple dose clinical trial of historic deacetylase inhibitor ITF2357 in patients with relapsed or progressive multiple myeloma: Preliminary results"; *Blood*, vol. 110, No. 11, Part 1, pp. 356A (2007) STN 2008:216406 BIOSIS.
Guerini, Vittoria, et al; "Potent inhibition of EEC Colony Formation in $JAK2^{V617F}$ PV and ET by Low Doses of ITF2357, a New Histone Deacetylase Inhibitor"; *Blood*, (ASH Annual Meeting Abstracts), vol. 108, No. 11, Part 1, 3 pgs. (2006).
Guerini, V., et al; "The histone deace6tylase inhibitor ITF2357 selectively targets cells bearing mutated $JAK2^{V617F}$"; *Leukemia*, vol. 22, No. 4, pp. 740-747 (2008) XP008114983.
Guerini, Vittoria, et al; "Selective Targeting of the $JAK2^{V617F}$ Mutation in Polycythemia Vera and Essential Thrombocythemia by ITF2357, a Novel Histone Deacetylase Inhibitior"; *Blood*, vol. 110, No. 11, Part 1, 3 pgs. (2007).
Fathallah, H., et al; "Induction of Fetal Hemoglobin in the Treatment of Sickle Cell Disease"; *American Society of Hematology*, pp. 58-62 (2006).
Silver, R.T.; "Treatment of Polycythemia Vera"; *Seminars in Thrombosis and Hemostasis*, vol. 32, No. 4, pp. 437-442 (2006).
Mesa, et al; "Bortezomib therapy in myelofibrosis: a phase II clinical trial"; *Leukemia*, vol. 22, pp. 1636-1638 (2008).
Quintas-Cardama, A., et al; "A phase II study of 5-azacitidine for patients with primary and post-essential thrombocythemia/polycythemia vera myelofibrosis"; *Leukemia*, vol. 22, pp. 965-970 (2008).
Berk, P.D., et al; "Increase Incidence of Acute Leukemia in Polycythemia Vera Associated with Chlorambucil Therapy"; *The New England Journal of Medicine*, vol. 304, No. 8, pp. 441-447 (1981).
James, C., et al; "A unique clonal *JAK2* mutation leading to constitutive signaling causes polycythaemia vera"; *Nature*, vol. 34, pp. 1144-1148 (2005).
Butler, L.M., et al; "Suberoylanilide Hydroxamic Acid, an Inhibitor of Histone Deacetylase, Suppresses the Growth of Prostate Cancer Cells in Vitro and in Vivo[1]"; *Cancer Research*, vol. 60, pp. 5165-5170 (2000).
Kralovics, R., et al; "A Gain-of-Function Mutation of *JAK2* in Myeloproliferative Disorders"; *The New England Journal of Medicine*, vol. 352, pp. 1779-90 (2005).
Blanchard, F., et al; "Histone deacetylase inhibitors: new drugs for the treatment of inflammatory diseases?"; *Drug Discovery Today*, vol. 10, No. 3, pp. 197-204 (2005).

(Continued)

*Primary Examiner* — Kendra D Carter
(74) *Attorney, Agent, or Firm* — Nixon & Vanderhye P.C.

(57) ABSTRACT

Method of treating Philadelphia-negative myeloproliferative syndromes in a patient suffering from such syndromes. The method is carried out by administering to the patient diethyl-[6-(4-hydroxycarbamoyl-phenylcarbamoyloxymethyl)-naphthalen-2-yl -methyl]-ammonium chloride, or other pharmaceutically acceptable salts and/or solvates, in a daily dosage amount of from 10 to 150 mg per patient.

9 Claims, No Drawings

(56) References Cited

OTHER PUBLICATIONS

Adcock, Im; "HDAC inhibitors as anti-inflammatory agents"; *British Journal of Pharmacology*, vol. 150, pp. 829-831 (2007).
Bi, G., et al; "The Molecular Mechanism of HDAC Inhibitors in Anticancer Effects"; *Cellular & Molecular Immunology*, vol. 3, No. 4, pp. 285-290 (2006).
Guerini, V., et al; "The histone deacetylase inhibitor ITF2357 selectively targets cells bearing mutated JAK2$^{V617F}$"; *Leukemia*, pp. 1-8 (2007).
Yoshida, M., et al; "Potent and Specific Inhibition of Mammalian Histone Deacetylase Both in Vivo and in Vitro by Trichostatin A*"; *The Journal of Biological Chemistry*; vol. 265, No. 28, pp. 17174-17179 (1990).
Paris, M., et al; "Histone Deacetylase Inhibitors: From Bench to Clinic"; *Journal of Medicinal Chemistry*; vol. 51, No. 6, pp. 1505-1529 (2008).
Marks, P.A., et al; "Histone Deacetylase Inhibitors: Inducers of Differentiation or Apoptosis of Transformed Cells"; *Journal of the National Cancer Institute*, vol. 92, No. 15, pp. 1210-1215 (2000).
Richon, V.M., et al; "A class of hydrib polar inducers of transformed cell differentiation inhibits histone deacetylases"; *Proc. Natl. Acad. Sci.*, vol. 95, pp. 3003-3007 (1998).
Leoni, F., et al; "The Histone Deacetylase Inhibitor ITF2357 Reduces Production of Pro-Inflammatory Cytokines in Vitro and Systemic Inflammation in Vivo"; *Molecular Medicine*, vol. 11, No. 1-12, pp. 1-15 (2005).
Najean, Y., et al; "Treatment of Polycythemia Vera: The Use of Hydroxyurea and Pipobroman in 292 Patients Under the Age of 65 Years"; *Blood*, vol. 90, p. 3370-3377 (1997).
Tutaeva, V., et al; "Application of PRV-1 mRNA expression level and JAK2V617F mutation for the differentiating between polycytemia vera and secondary erythrocytosis and assessment of treatment by interferon or hydroxyurea"; *Hematology*, vol. 12, No. 6, pp. 473-479 (2007).
Barosi, G., et al; "Response criteria for essential thrombocythemia and polycythemia vera: result of a European LeukemiaNet consensus conference"; *Blood*, vol. 113; pp. 4829-4833 (2009).
Johansson, P., et al; "The effects of hydroxyurea on *PRV-1* expression in patients with essential thrombocythemia and polychtmia vera"; *Haematologica*, vol. 89, No. 10, pp. 1264-1266 (2004).
Jones, P., et al; "A Novel Series of Potent and Selective Ketone Histone Deacetylase Inhibitors with Antitumor Activity in Vivo"; *J. Med. Chem.*, vol. 51, pp. 2350-2353 (2008).
Martin, et al; "HEL Cells: A New Human Erythroleukemia Cell Line with Spontaneous and Induced Globin Expression"; *Science*, vol. 216, pp. 1233-1235, XP008160201 (1982).
Bonfante, V., et al; "Phase II Study of the Histone-Deacetylase Inhibitor *ITF2357* in Relapsed/Refradtory Hodgkin's Lymphoma Patients"; *Haematologica*, vol. 93(s1), p. 244, XP008160204 (2008).
Vojinovic, J., et al; "Presentation: Safety and Efficacy of Oral ITF 2357 in Patients with Active Systemic Onset Juvenile Idiopathic Arthritis (SOJIA)—Results of a Phase II, Open Label, International, Multicentre Clinical Trial"; *American College of Rheumatology, 2008 Annual Scientific Meeting*; 1 pg, XP008160205 (2008).
Uozumi, K., et al; "Establishment and characterization of a new human megakaryoblastic cell line (SET-2) that spontaneously matures to megakaryocytes and produces platelet-like particles"; *Leukemia*, vol. 14, pp. 142-152 (2000).
Guerini, V., et al; 12$^{th}$ Congress of the European Hematology Association, Jun. 7-10, 2007; "Potent and Selective Inhibition of EEC Colony Formation in JAK2V617F Polycythemia Vera and Thrombocythemia by Low Doses of ITF2357, A New Histone Deacetylase Inhibitor"; *Heamatologica 2007*; [suppl. 2]:89, Abstract 0245; http://online.haematologica.org/eha12/browserecord_prt.php?-action=browse&-recid, p. 1 of 1; dated Apr. 2, 2016.
Prchal, J.T.; "Philadelphia Chromosome-Negative Myeloproliferative Disorders: An Historical Perspective"; *American Society of Hematology*, p. 68 (Jan. 1, 2008).

* cited by examiner

USE OF HISTONE DEACETYLASE INHIBITORS FOR THE CARE OF PHILADELPHIA-NEGATIVE MYELOPROLIFERATIVE SYNDROMES

This application is a continuation of U.S. patent application Ser. No. 13/064,450 filed Mar. 25, 2011, abandoned, which is a continuation of PCT/EP2009/062214, filed Sep. 21, 2009, which claims priority to Italian Patent Application No. MI2008A001720, filed Sep. 29, 2008 and claims benefit of U.S. Provisional Patent Application No. 61/193,283, filed Nov. 13, 2008, the entire contents of each of which are hereby incorporated by reference.

Myeloproliferative syndromes are disorders of the neoplastic type which have in common the fact that they originate from pluripotent stem cells from bone marrow, that is to say, cells which, by dividing, can form various types of blood cell.

Myeloproliferative syndromes are separated into four types: chronic myeloid leukaemia (CML), polycythemia vera (PV), essential thrombocythemia (ET), and idiopathic myelofibrosis (IM).

The molecular basis for chronic myeloid leukaemia has been known for some time and consists in the formation of the Philadelphia chromosome, or the 9;22 translocation, and the generation of the BCR-ABL fusion gene; in these cases, called Philadelphia-positive myeloproliferative syndromes, the use of a specific ABL tyrosine kinase inhibitor (such as imitinib or desatinib) makes it possible to intervene selectively in the cells responsible for the pathology, limiting the possible consequences of a non-specific cytotoxicity to the detriment of the healthy cells.

For the other three pathologies, grouped under the name of Philadelphia-negative myeloproliferative syndromes, the molecular basis has been identified more recently [see, for example: Robert Kralovics et al. in *The New England Journal of Medicine* 352, 1779-1790 (2005); Chloé James et al. in *Nature* 434, 1144-1148 (2005)] and seems to relate to a gene mutation affecting JAK2 tyrosine kinase. For these syndromes, current therapy also provides for the use of cytostatic drugs having a non-specific action, principally hydroxyurea, which present a risk of inducing, after a certain period of treatment, the development of pathologies towards myelodysplastic states and towards forms of leukaemia. In Europe, the incidence of Philadelphia-negative myeloproliferative syndromes is approximately 5 cases for every 100,000 inhabitants per year.

It is therefore clear that it is necessary to identify new drugs which, even for Philadelphia-negative myeloproliferative syndromes (PV, ET and IM), can act in a more selective manner and at non-toxic doses.

Histone deacetylases (HDAC) are enzymes capable of removing the acetyl group bound to the lysine residues in the N-terminal portion of histones or in other proteins.

HDACs can be subdivided into four classes, on the basis of structural homologies. Class I HDACs (HDAC 1, 2, 3 and 8) are similar to the RPD3 yeast protein and are located in the cell nucleus. Class II HDACs (HDAC 4, 5, 6, 7, 9 and 10) are similar to the HDA1 yeast protein and are located both in the nucleus and in the cytoplasm. Class III HDACs are a structurally distinct form of NAD-dependent enzymes correlated with the SIR2 yeast protein. Class IV (HDAC 11) consists at the moment of a single enzyme having particular structural characteristics. The HDACs of classes I, II and IV are zinc enzymes and can be inhibited by various classes of molecule: hydroxamic acid derivatives, cyclic tetrapeptides, short-chain fatty acids, aminobenzamides, derivatives of electrophilic ketones, and the like. Class III HDACs are not inhibited by hydroxamic acids, and their inhibitors have structural characteristics different from those of the other classes.

The expression "histone deacetylase inhibitor" in relation to the present invention is to be understood as meaning any molecule of natural, recombinant or synthetic origin capable of inhibiting the activity of at least one of the enzymes classified as histone deacetylases of class I, class II or class IV.

Histone deacetylase inhibitors are a class of molecules provided with anti-neoplastic and anti-inflammatory activity.

In tumour cells, histone deacetylase inhibitors inhibit cell proliferation and induce cell death and differentiation [Gaofeng Bi and Guosheng Jiang in *Cellular & Molecular Immunology* 3, 285-290 (2006)].

Histone deacetylase inhibitors are also capable of modulating the production of cytokines and other pro-inflammatory factors on the part of immuno-competent cells and have demonstrated, in vivo, anti-inflammatory properties [Frederic Blanchard and Celine Chipoy in *Drug Discovery Today* 10, 197-204 (2005); IM Adcock in *British Journal of Pharmacology* 150, 829-831(2007)].

Numerous clinical studies, both on tumour pathologies and on inflammatory pathologies, are currently underway, and are at various stages of advance, using various inhibitors [Marielle Paris et al., in *Journal of Medicinal Chemistry* 51, 1505-1529 (2008)].

Recently, a histone deacetylase inhibitor (Zolinza, vorinostat) has been approved for the treatment of cutaneous T-cell lymphoma.

Some of the histone deacetylase inhibitors currently at the clinical study stage are described, with other analogues thereof, in the following patents: WO 2004/092115, WO 2005/019174, WO 2003/076422, WO 1997/043251, WO 2006/010750, WO 2006/003068, WO 2002/030879, WO 2002/022577, WO 1993/007148, WO 2008/033747, WO 2004/069823, EP 0847992 and WO 2004/071400, the contents of which are incorporated herein by reference in their entirety.

Diethyl-[6-(4-hydroxycarbamoyl-phenylcarbamoyloxymethyl)-naphthalen-2-yl methyl]-ammonium chloride, which is described in WO 97/43251 (anhydrous form) and in WO 2004/065355 (monohydrate crystal form), herein both incorporated by reference, is an HDAC inhibitor with good anti-inflammatory activities; such an active principle is also known as ITF2357 and/or Givinostat. In lipopolysaccharide (LPS)-stimulated cultured human peripheral blood mononuclear cells (PBMCs), ITF2357 reduced by 50% the release of tumor necrosis factor-α (TNFα) at 10 to 22 nM, the release of intracellular interleukin (IL)-1α at 12 nM, the secretion of IL-1β at 12.5 to 25 nM, and the production of interferon-γ (IFNγ) at 25 nM. Oral administration of 1.0 to 10 mg/kg ITF2357 to mice reduced LPS-induced serum TNFα and IFNγ by more than 50% [Flavio Leoni et al. in *Molecular Medicine* 11, 1-15 (2005)].

It has recently been reported that ITF2357, at sub-micromolar concentrations, is capable of inhibiting the clonogenic activity of stem cells obtained from patients suffering from PV or ET [V. Guerini et al. *Leukemia* 22, 740-747 (2008)]. However, the concentrations at which inhibition of clonogenic activity is obtained are much lower than those necessary for obtaining a modification of the molecular markers (JAK2$^{V617F}$ and STAT proteins) or a cytotoxic effect; the ambiguity of these results makes it difficult to provide for the transferability of these effects, obtained in vitro, to situations of treatment in vivo, especially for any therapeutic treatments in humans.

DESCRIPTION OF THE INVENTION

We have now found, and this constitutes one aspect of the present invention, that the administration of diethyl-[6-(4- hydroxycarbamoyl-phenylcarbamoyloxymethyl)-naphthalen-2-yl methyl]-ammonium chloride, preferably in monohydrate form, more preferably in monohydrate crystal form, to patients suffering from polycythemia vera, essential thrombocythemia or myelo fibrosis causes a complete or partial response; in addition, in patients who initally demonstrated a state of splenomegaly, a significant reduction in the volume of the spleen is observed.

We have also found, and this constitutes a second aspect of the invention, that the therapeutic dose of such an active principle, for the treatment of Philadelphia-negative myeloproliferative syndromes in humans, is significantly lower than that normally used for the care of tumour syndromes and may be from 10 to 150 mg/day/patient, preferably from 30 to 120 mg/day/patient, and even more preferably from 50 to 100 mg/day/patient.

Purely by way of example, the dose of Zolinza™ (vorinostat) indicated for the treatment of cutaneous T-cell lymphoma is 400 mg/day.

The present invention relates to the use of diethyl-[6-(4-hydroxycarbamoyl-phenylcarbamoyloxymethyl)-naphthalen-2-yl methyl]-ammonium chloride, preferably in monohydrate form, more preferably in monohydrate crystal form for the therapeutic treatment of Philadelphia-negative myeloproliferative syndromes (polycythemia vera, essential thrombocythemia or idiopathic myelofibrosis). Such an active principle may be used alone, i.e. not in combination with other active principles, or in combination with other cytostatic active principles such as, purely by way of example, hydroxyurea or pipobroman.

The present invention relates also to the therapeutic use of such an active principle, for the treatment of Philadelphia-negative myeloproliferative syndromes, at daily doses lower than those used for the treatment of tumour pathologies (for example: cutaneous T-cell lymphoma), these doses being from 10 to 150 mg/day/patient, preferably from 30 to 120 mg/day/patient, and even more preferably from 50 to 100 mg/day/patient.

The term "treatment", in relation to the present invention, is to be understood as meaning the action of caring for, relieving, mitigating, minimizing, eliminating or blocking the harmful effects resulting from the pathological state or the progression of the disease.

The inhibitory activity of a particular compound, with respect to histone deacetylases, may be measured in vitro using, for example, an enzyme test which demonstrates the inhibition of at least one of these enzymes. Tests of this type are known in the literature: see, for example, P. A. Marks et al. in *J. Natl. Cancer Inst.* 92 1210-1215 (2000); L. M. Butler et al. in *Cancer Res.* 60 5165-5170 (2000); V. M. Richon et al. in *Proc. Natl. Acad. Sci.* USA 95 3003-3007 (1998); M. Yoshida et al. in *J. Biol. Chem.* 265 17174-17179 (1990); kits for measuring the HDAC inhibition are also available commercially (e.g. Biomol International LP (USA); HDAC1 Fluorimetric Drug Discovery Kit, product number BML-AK511-0001).

The following examples are intended to be illustrative of the invention rather than limiting the scope thereof.

EXAMPLE 1

Clinical study of ITF2357 in patients suffering from Philadelphia-negative myeloproliferative syndromes. Design: phase II, open, non-randomized study. Population in the study: 27 patients with the JAK2$^{V617F}$ mutation suffering from myeloproliferative syndromes not adequately controlled by the standard pharmacological treatment (hydroxyurea).

Drug under study: ITF2357 at a dose of 50 mg twice per day.

Duration of the treatment: up to a maximum of 24 weeks of continual administration.

Primary objective: to evaluate the efficiency and tolerability of ITF2357 in the treatment of patients having JAK2$^{V617F}$-positive myeloproliferative diseases (PV, ET, IM).

Secondary objective: to evaluate the effect of the treatment on the mutated JAK2 allele burden by quantitative PCR.

Examination of the preliminary data (duration of the treatment from 4 to 12 weeks) shows that the administration of ITF2357 to patients suffering from polycythemia vera, essential thrombocythemia or myelofibrosis induces a complete or partial response in approximately 60% of cases; in addition, a significant reduction in the volume of the spleen is observed in patients who initially exhibited a state of splenomegaly.

EXAMPLE 2

Comparative Effect on the Cloning Efficiency of the Human Cell Line SET-2

The JAK2$^{V617F}$ mutated, human cell line SET-2 (a megakaryoblastic cell line established from the peripheral blood of a patient with leukemic transformation of essential thrombocythemia) was obtained by the German cell bank DSMZ (catalogue number ACC 608) and grown in 24 well plates in culture medium (RPMI 1640+Hepes buffer 1M+Penicillin 10.000 IU/ml+Streptomycin 10,000 µg/ml+20% foetal calf serum). Previous experiments were carried out to determine the optimal number of cells giving a sufficient number of clones in each Petri dish to make a reproducible counting. In the case of the SET-2 line the number corresponded to 3×10$^3$ cells/Petri dish. When a sufficient number of cells were obtained, the cells were harvested by centrifugation (10 min at 10$^3$ rpm) and then suspended in culture medium at the concentration of 90×10$^3$ cells/ml. 100 µl of the suspension were added to 3.0 ml of methyl-cellulose (Methocult™, catalogue number H4230, Stemcell Technologies) prepared as described by manufacturer and, then, 50 µl of 63 fold concentrated solution of the HDAC inhibitor in 0.1% DMSO was added. For each compound 5 serial dilutions (1000-12 nM range) were tested. The methyl-cellulose solution containing the HDAC inhibitor was then carefully mixed using a sterile plastic Pasteur pipette avoiding the formation of bubbles. At the end 1 ml of the solution was homogeneously dispensed in a Petri dish (35 mm diameter with grid, catalogue number 174926 Nunc) using a syringe with a 18G needle. For each experimental point 2 Petri dishes were done. The 2 experimental dishes were put in an larger Petri dish along with a reservoir of sterile water to ensure a constant humidity. All the dishes were then maintained at 37° C. in a humidity and CO$_2$-controlled sterile incubator. After 14 days of growing the number of clones in each dish was determined by using a binocular microscope. The average number of clones for each coupe of dishes was calculated and the percentage inhibition of clones formation was determined in respect to the number of clones obtained in the absence of any compounds (control dishes). The EC$_{50}$ value (concentration required to reduce of 50% the number of clones) was calculated using GraphPad Prism 5.0 software and reported in the table below. Values for rhHDAC1 inhibition are also reported: the enzyme was obtained from BPS Biosciences (cat n. 50001) and the test was carried out using a BIOMOL kit, according to supplier instructions.

TABLE 1

| Code | Originator | INN | Chemical Class | EC$_{50}$ µM | IC$_{50}$ nM (rhHDAC1) |
|---|---|---|---|---|---|
| ITF2357 | Italfarmaco | Givinostat | Hydroxamic acid | 0.028-0.054* | 121 |
| MGCD-0103 | MethylGene | Mocetinostat | Benzamide | 1.196** | 17 |
| KD-5170 | Kalypsys | — | S,Acetyl-α-mercaptoketone | <20% inhib. at 1 µM | 24 |
| SNDX-275 | Bayer Schering | Entinostat | Benzamide | 1.820** | 293 |

*values obtained in two different experiment
**p < 0.05 towards ITF2357 in the same experiment Although Mocetinostat and Entinostat are considered as class I specific HDAC inhibitors [Zhou, N. et al. *J Med Chem* 51, 4072 (2008) and Jones, P. et al. *J Med Chem* 51, 2350 (2008)], KD-5170 has been reported to be a broad spectrum Class I and II-HDAC inhibitor [WO 2007/067795; Payne, J. E. et al. *Bioorg Med Chem Lett* 18, 6093 (2008)], the same as ITF2357.

Although, the inhibition of cloning efficiency of SET-2 cells is not proven to be predictive for the cure of the Philadelphia-negative, JAK2$^{V617F}$-positive, myeloproliferative syndromes, the potent inhibitory effect of ITF2357, if compared to the other HDAC inhibitors, seems to indicate that the presence of histone deacetylase inhibition is not essential for obtaining the clinical efficacy shown by ITF2357 with respect to Philadelphia-negative myeloproliferative syndromes.

The tested compounds correspond to the following formulae:

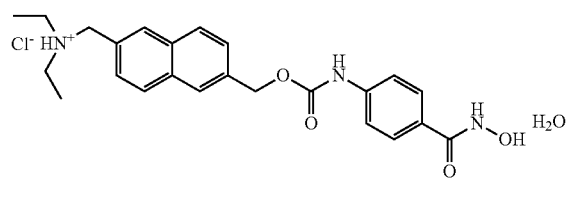

Givinostat (ITF2357)

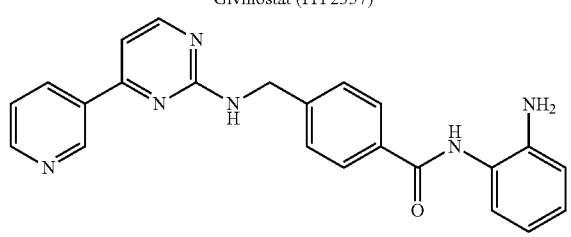

Mocetinostat (MGCD-0103)

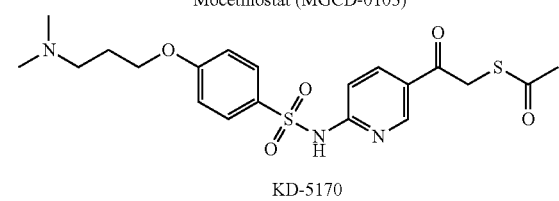

KD-5170

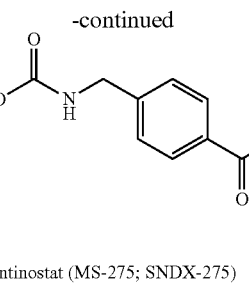

Entinostat (MS-275; SNDX-275)

The invention claimed is:

1. Method of treating Philadelphia-negative myeloproliferative syndromes in a patient suffering from said syndromes, said method comprising administering to said patient diethyl-[6-(4-hydroxycarbamoyl-phenylcarbamoyloxymethyl)-naphthalen-2-yl-methyl]-ammonium chloride, or other pharmaceutically acceptable salts and/or solvates, and at least one other cytostatic active principle, wherein said diethyl-[6-(4-hydroxycarbamoyl-phenylcarbamoyloxymethyl)-naphthalen-2-yl-methyl]-ammonium chloride, or other pharmaceutically acceptable salts and/or solvates thereof is administered in a daily dosage amount of from 50 to 150 mg per patient.

2. Method according to claim 1, wherein said diethyl-[6-(4-hydroxycarbamoyl-phenylcarbamoyloxymethyl)-naphthalen-2-yl-methyl]-ammonium chloride is in monohydrate form.

3. Method according to claim 1, wherein said diethyl[6-(4-hydroxycarbamoyl-phenylcarbamoyloxymethyl)-naphthalen-2-yl-methyl]-ammonium chloride is in monohydrate crystal form.

4. Method according to claim 1, wherein said Philadelphia-negative myeloproliferative syndrome is polycythemia vera.

5. Method according to claim 1, wherein said Philadelphia-negative myeloproliferative syndrome is essential thrombocythemia.

6. Method according to claim 1, wherein said Philadelphia-negative myeloproliferative syndrome is primary myeofibrosis.

7. Method according to claim 1, wherein said Philadelphia-negative myeloproliferative syndrome is secondary myelofibrosis.

8. Method according to claim 1, wherein said at least one other cytostatic active principle is selected from the group consisting of hydroxyurea and pipobroman.

9. Method according to claim 1, wherein said daily dosage is from 50 to 100 mg per patient.

* * * * *